United States Patent [19]

Rush et al.

[11] Patent Number: 4,457,162

[45] Date of Patent: Jul. 3, 1984

[54] MULTI-FREQUENCY PHOTO-ACOUSTIC DETECTOR

[75] Inventors: William F. Rush, Tinley Park; James E. Huebler, Brookfield, both of Ill.

[73] Assignee: Institute of Gas Technology, Chicago, Ill.

[21] Appl. No.: 419,231

[22] Filed: Sep. 17, 1982

[51] Int. Cl.$^3$ ............................................. G01N 21/17
[52] U.S. Cl. ....................................................... 73/24
[58] Field of Search ..................... 73/24, 592; 250/345

[56] References Cited

U.S. PATENT DOCUMENTS

| | | | |
|---|---|---|---|
| 3,938,365 | 2/1976 | Dewey, Jr. | 73/24 |
| 3,948,345 | 4/1976 | Rosencwaig | 73/24 X |
| 4,176,963 | 12/1979 | Fabinski | 250/345 X |

FOREIGN PATENT DOCUMENTS 1442168 7/1976 United Kingdom ................ 250/345

OTHER PUBLICATIONS

Nitric Oxide Air Pollution: Detection by Optoacoustic Spectroscopy, Kreuzer, Patel, Science, vol. 173, pp. 45-47.

Primary Examiner—Gerald Goldberg
Assistant Examiner—Vince Kovalick
Attorney, Agent, or Firm—Thomas W. Speckman

[57] ABSTRACT

An apparatus and process for detecting a single specific chemical solid or gas in the presence of other chemical solids or gases or for detecting a number of specific mixed chemical solids or gases. The apparatus and process passes multiple beams of electromagnetic radiation incident on the material in a sample chamber producing acoustic signals at specific frequencies when light of specific wavelengths is absorbed. The electromagnetic radiation is selected to have wavelengths corresponding to optical absorption features of at least one specific chemical in the sample chamber. The acoustic signals are detected by at least one beat tone or combination tone characteristic of and representative of the degree of absorption by a specific chemical or multiple specific chemicals desired to be detected. The apparatus and process are especially useful in leak detection in natural gas systems and for detection of pollutants, explosive gases and the like.

25 Claims, 1 Drawing Figure

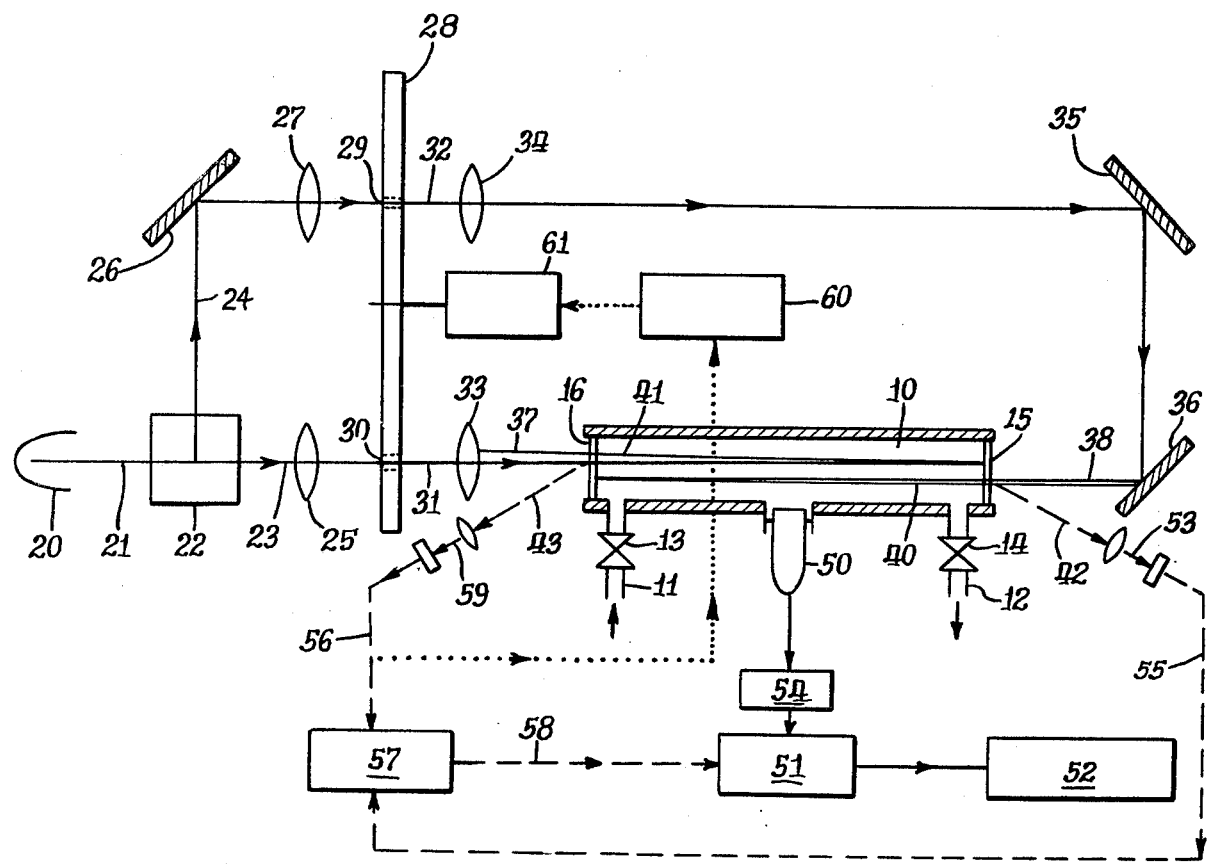

MULTI-FREQUENCY PHOTO-ACOUSTIC DETECTOR

BACKGROUND OF THE INVENTION

1. Field of the Invention

This invention relates to apparatus and process for detecting a single specific chemical solid or gas in the presence of other chemical solids or gases or for detecting a number of specific mixed chemical solids or gases. The apparatus and process is particularly suitable for detecting a single specific gas in the presence of other gases or for detecting a number of specific mixed gases. The apparatus and process passes multiple beams of electromagnetic radiation incident on the material, such as gases, in a sample chamber producing acoustic signals at specific frequencies when the light of specific wavelengths is absorbed. The electromagnetic radiation is selected to have wavelengths corresponding to optical absorption features of a single specific chemical or a number of specific mixed chemicals in the sample chamber. The acoustic signals are detected by a beat tone or a combination tone characteristic of and representative of the degree of absorption by the specific chemical or multiple specific chemicals desired to be detected in the sample. The apparatus and process are useful in leak detection in natural gas systems and chemical processes and for detection of pollutants, explosive gases and the like.

2. Description of the Prior Art

The need to detect a specific chemical, such as gas, or a mixture of specific chemicals, such as gases, in a sample, such as a gas stream, frequently arises and a number of detection techniques have been devised. One frequent need for detection of a single specific gas arises in connection with location of leaks in natural gas systems, in the detection of pollutants, poison or explosive gases. Many of the gas detection techniques currently available do not provide desired specificity and are not suitable for field use. For example, currently used devices for leak survey in natural gas pipelines include combustible gas indicators and flame ionization detectors, both of which are incapable of distinguishing methane from a methane-ethane mixture, and gas chromatographs which do make such distinctions, but are not practical for field utilization.

Various sonic leak detectors have been proposed which do not detect a single specific gas, such as: U.S. Pat. No. 3,055,209 teaching an active sonic leak detector by transmitting sonic waves through the gas within a conduit and through the leak opening for detection; and U.S. Pat. No. 3,264,864 teaching transmission of a sonic wave of one frequency through a gas conduit and detecting a mechanical wave of sonic frequency transmitted by the gas through a leak in the conduit. Acoustic means have been used to detect specific gases. U.S. Pat. No. 3,429,177 teaches hydrogen gas detection by change of velocity of specific wavelength acoustic waves in passing through the hydrogen; U.S. Pat. No. 3,981,176 teaches determination of gas composition by measurement of acoustic impedance and absorption of gas at two distinct frequencies; and U.S. Pat. No. 4,246,773 which teaches determination of specific gravity of a gas by determining the sonic speed in the gas by electrical measurement of a beat frequency obtained by mixing the output of an acoustic detector wherein the sound is passed through a standard gas with the output of a detector in which the sound is passed through the gas in question. U.S. Pat. No. 3,938,365 teaches detection of trace amounts of one gaseous species in a sample chamber acoustically in response to a high intensity light source having its beam modulated at a frequency corresponding to an acoustical resonant frequency of the sample chamber. The photoelectric and acoustical signal leaving the sample chamber are compared and the acoustical signal provides an indication of energy absorbed by the gas in the sample chamber at the light wavelength. The process taught by the '365 patent allows only identification of a single gas species.

The prior art does not, to the inventors' knowledge, suggest any devices capable of detecting multiple specific gases in a mixture of specific gases nor any devices capable of detecting a specific gas in the presence of other gases which absorb the same electromagnetic wavelengths.

SUMMARY OF THE INVENTION

The present invention provides apparatus and process for detection of a single specific gas or solid in the presence of other gases or solids, and for detection of multiple specific gases or solids in a mixture. The apparatus and process utilizes electromagnetic radiation corresponding to a characteristic absorbed wavelength of at least one of the chemical materials making up the specific gas or solid or multiple specific gases or solids to be detected in a sample chamber. The multiple beams of electromagnetic radiation modulated in the above fashion are incident on gases or solids in the sample chamber producing acoustic signals at specific frequencies when the light beams of specific wavelengths are absorbed. The acoustic signals are detected by at least one beat tone or at least one combination tone characteristic of and representative of the degree of absorption by the specific gas or solid or multiple specific gases or solids desired to be detected in the sample.

It is an object of this invention to provide a multi-frequency photo-acoustic gas or solid detector system capable of detecting a number of specific mixed gases or solids.

It is another object of this invention to provide a multi-frequency photo-acoustic gas or solid detection system for detecting a single specific gas or solid in the presence of other gases or solids which may absorb the same electromagnetic wavelengths.

It is still another object of this invention to provide a photo-acoustic gas or solid detection system utilizing multiple optical wavelengths, each of which is modulated to produce a specific acoustic signal at a specific frequency characteristic of absorption of that light beam by a specific chemical.

It is yet another object of this invention to provide a multi-frequency photo-acoustic gas detection system the acoustical detection system of which detects a beat tone or a combination tone characteristic and representative of the degree of absorption of electromagnetic radiation by the specific gas or solid or multiple specific gases or solids desired to be detected.

It is yet another object of this invention to provide a photo-acoustic gas detector system for use in detecting natural gas and distinguishing methane and ethane in such natural gas in a single measurement system.

BRIEF DESCRIPTION OF THE DRAWING

The above and other objects, advantages and features of this invention will be apparent from the description together with the drawing wherein:

The FIGURE schematically shows in a block diagram the components of a multi-frequency photoacoustic gas detector system according to one embodiment of this invention.

DESCRIPTION OF PREFERRED EMBODIMENTS

Referring to the FIGURE, a two-frequency photoacoustic gas detector is shown having sample chamber 10 provided with inlet 11 and outlet 12 controlled by valve 13 and valve 14, respectively. Solid or gaseous materials to be detected may be placed in sample chamber 10. Collimated light source 20 provides collimated light beam 21 to light beam splitter 22 which divides collimated light beam 21 into two, not necessarily equal, split light beams 23 and 24. Split light beam 24 is directed by mirror 26 to focusing lens 27 and split light beam 23 passes directly to focusing lens 25 for passage through holes 29 and 30, respectively, in light chopper blade 28. Light chopper blade 28 has one set of holes 29 and a second set of holes 30 at different radii and each set of holes has a different number of holes around the circle made by its rotation thereby upon rotation chopping each of the split light beams 23 and 24 at a different acoustic frequency. After the light beams are chopped at frequencies corresponding to the chopper blade set of holes the light beam passes through, each chopped light beam 31 and 32 is recollimated by recollimation lens 33 and 34, respectively. Each recollimated, chopped light beam is passed through a thin film interference filter 15 or 16 in the end of sample chamber 10. Each of the interference filters passes nearly monochromatic wavelengths of light chopped at a different acoustic frequency. The interior of sample chamber 10 is thereby irradiated by two different nearly monochromatic optical wavelengths of light. The modulated optical wavelengths are chosen to correspond to resonant wavelengths of a single specific gas or solid or a number of specific mixed gases or solids in the sample chamber. As the specific materials absorb the modulated light beams, a sound is generated at corresponding frequencies. Thus, two acoustical signals at different frequencies are produced within the sample chamber shown in the FIGURE.

The acoustical signals produced in the sample chamber are detected by sonic detector 50, such as a microphone, and transmitted as electrical signals through non-linear element 54 to signal detector 51. Signal detector 51, such as a lock-in amplifier, is adjusted to detect the beat signal or the combination signal, the subtractive of the additive signal, respectively, corresponding to absorption of the specific acoustical wavelengths by the gas or solid in the sample chamber. For example, if one of the essentially monochromatic light beams is absorbed only by methane and the other essentially monochromatic light beam is absorbed only by ethane, the signal detector will respond only to a combination of methane and ethane. The presence of methane or ethane alone will not produce a signal which is detected by the signal detector. The specificity of the detector of this invention for detection of a single specific gas may be enhanced by selecting two essentially monochromatic light beams at two different wavelengths absorbed by the one specific gas. In this detection of a single specific gas, the detector will respond only if the gas in the sample chamber absorbs both of the optical wavelengths absorbed by that specific gas.

Reflected light beams 42 and 43 represent light reflected from interference filter 15 and 16, respectively. Each reflected light beam 42 and 43 is detected by photodiodes 53 and 59, respectively, producing a corresponding electrical signal 55 and 56, respectively, which is fed to reflected light signal mixer 57 where it is electronically mixed to produce a beat or combination signal which is used as a reference signal by signal detector 51. The electrical signal produced by either photodiode, or the beat or combination signal produced by reflected signal mixer 57 may be used to control chopper motor 61 by passage to rotation rate stabilizer 60. The output of signal detector 51 may be supplied to any suitable recording or readout means 52.

The detection system can be simplified by use of light sources which produce a very narrow wavelength beam, such as lasers, thereby omitting the need for focusing and recollimating lenses and permitting direct chopping of the beam. In some cases, sufficiently collimated light sources are available, including lasers which are pumped by light sources at specified wavelengths, which permit operation of the sample chamber without the need for light beam interference filters 15 and 16, but require only a sample chamber window. In such cases, two light beams may enter the same chamber window and the reference signal is generated by electrically mixing the generated signals in mixer 57.

Suitable sources of electromagnetic radiation for use as a collimated light source in this invention include incandescent sources, arc sources, light-emitting diodes, infrared-emitting diodes, and laser sources.

The electromagnetic radiation may be modulated by the originating source, such as an intensity-modulated laser, or a light-emitting diode or infrared-emitting diode that is rapidly switched on and off or by mechanical means such as rotating choppers. Narrow bands of wavelengths may be provided by these same sources or by light beam interference filters, such as commercially available Fabry-Perot dielectric interference filters for isolation of the electromagnetic radiation to the desired wavelength for passage through the sample chamber.

A mechanical chopper, such as a rotating chopper, may be controlled to the desired rotational velocity by analysis of its output beams by methods readily known in the art.

Detection of the acoustical signal generated in the sample chamber may be made by a microphone in the chamber wall for conversion of the acoustical signal to an electrical signal. The electrical signal so produced and detected by the signal detector must be non-linear if beat or combination signals are to be detected. For example, use of low quality electronics for which output is a non-linear function of the input signal, will produce electrical beat signals. However, it may be desired to deliberately include a non-linear electronic element in the analysis system. Suitable non-linear elements include resistance-capacitance integrating circuits or modulation-envelope follower circuits such as an alternating current root-mean-square to d.c. voltage converter circuit. The non-linear element can be adjusted to respond to frequencies only below a user selected value. Likewise, a resistance-capacitance integrating circuit can be used to pass frequencies below a selected value and to block frequencies above that value. Use of the non-linear element results in good detection of the beat and combination signals described above.

While the above description has described in detail operation of the process using two beams of light, it is readily apparent that more than two and up to about four to six beams may be used in the same manner. It is preferred to use two to about four beams of light. The multiple beams of light may be at wavelengths selected from absorption wavelengths of one specific chemical material to increase sensitivity of the apparatus and process for that specific chemical, especially when present in a mixture of chemicals having characteristic absorption wavelengths close to each other. The multiple beams of light may be at wavelengths selected from absorption wavelengths characteristic of multiple chemical materials allowing a single measurement to identify the presence of multiple chemical materials in the sample chamber.

In a specific example to illustrate the principles of this invention, a sample of carbon block was placed in a sample chamber and illuminated with two separate optical beams of white light. One beam was chopped at a frequency of 177 hz and the other was chopped at a frequency of 168 hz. The beams had powers of 250 and 300 watts, respectively. A microphone in the sample chamber wall produced an electrical signal of 0.1 volt which was amplified by a linear amplifier with a gain of 100 to produce an undistorted signal of 10 volts. The 10 volt signal was then fed to an alternating current root-mean-square to d.c. converter circuit having a response time constant of 25 milliseconds, corresponding to a frequency of 40 hz. When each of the optical beams was individually passed through the sample chamber, no signal was indicated because the frequencies of 168 hz and 177 hz were above the 40 hz frequency limit imposed by the converter. When both optical beams were simultaneously passed through the sample chamber, a 9 hz signal was observed at the output of the d.c. converter. The output signal represents the beat frequency which was below the 40 hz upper limit of the converter.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. A process for detecting a single specific gas or solid in a mixture or a number of specific mixed gases or solid materials comprising:
   passing said material to be detected into a sample chamber;
   modulating multiple beams of electromagnetic radiation having wavelengths corresponding to a characteristic absorbed wavelength of at least one of the chemicals in said material to be detected;
   simultaneously passing multiple beams of said modulated electromagnetic radiation incident on said material to be detected in said sample chamber causing multiple acoustical signals at specific frequencies upon absorption of said modulated beams of electromagnetic radiation; and
   detecting the acoustical signal corresponding to at least one beat tone or at least one combination tone characteristic of said specific material to be detected.

2. The process of claim 1 wherein 2 to 6 beams of electromagnetic radiation are used.

3. The process of claim 1 wherein 2 to 4 beams of electromagnetic radiation are used.

4. The process of claim 1 wherein said material to be detected is gaseous.

5. The process of claim 1 wherein said material to be detected is solid.

6. The process of claim 1 wherein said wavelengths of electromagnetic radiation correspond to multiple characteristic absorbed wavelengths of a single chemical material to be detected.

7. The process of claim 1 wherein each of said wavelengths of electromagnetic radiation corresponds to single characteristic absorbed wavelengths of different chemical materials to be detected.

8. The process of claim 1 wherein said electromagnetic radiation is modulated by passing through a mechanical chopper.

9. The process of claim 1 wherein said electromagnetic radiation is modulated by the originating source.

10. The process of claim 1 wherein said beams of electromagnetic radiation are produced by light sources emitting a narrow wavelength beam.

11. The process of claim 1 wherein said acoustical signal is passed through a non-linear electronic element prior to detection.

12. The process of claim 1 wherein at least one beat tone is detected.

13. The process of claim 1 wherein at least one combination tone is detected.

14. The process of claim 1 wherein said material to be detected is gaseous; two to four beams of said electromagnetic radiation are used; and said acoustical signal is passed through a non-linear electronic element prior to detection.

15. The process of claim 14 wherein at least one beat tone is detected.

16. The process of claim 14 wherein at least one combination tone is detected.

17. An apparatus for detecting a single specific gas or solid material in a mixture or a number of specific mixed gases or solid materials comprising:
   means defining a sample chamber for containing said material;
   means for generating at least one beam of electromagnetic radiation;
   means for simultaneously passing incident on said material in said sample chamber multiple beams of modulated electromagnetic radiation at wavelengths corresponding to a characteristic absorbed wavelength of at least one of the chemicals in said material to be detected;
   means for acoustical detection of multiple acoustical signals at specific frequencies upon absorption of said modulated beams of electromagnetic radiation providing an output electrical signal corresponding to a beat tone or a combination tone characteristic of said specific material or said number of specific mixed materials; and
   means for detection and indication of said output electrical signal.

18. The apparatus of claim 17 wherein said means for generating electromagnetic radiation comprises a laser source.

19. The apparatus of claim 17 wherein said means for generating electromagnetic radiation comprises an incandescent source.

20. The apparatus of claim 17 wherein said means for generating electromagnetic radiation comprises an arc source.

21. The apparatus of claim 17 wherein said means for generating electromagnetic radiation comprises an infrared source.

22. The apparatus of claim 17 additionally comprising a mechanical chopper for modulating said electromagnetic radiation.

23. The apparatus of claim 17 additionally comprising light beam interference filters for isolation of desired wavelength electromagnetic radiation.

24. The apparatus of claim 17 comprising a microphone in said sample chamber for acoustical detection.

25. The apparatus of claim 17 wherein said means for detection of said output electrical signal comprises at least one non-linear electronic element.

* * * * *